United States Patent

Williams

(10) Patent No.: US 6,506,958 B2
(45) Date of Patent: Jan. 14, 2003

(54) SIGNAL TAMPON

(75) Inventor: Karla E Williams, Westwood, NJ (US)

(73) Assignee: Playtex Products, Inc., Westport, CT (US)

(*) Notice: Subject to any disclaimer, the term of this patent is extended or adjusted under 35 U.S.C. 154(b) by 0 days.

(21) Appl. No.: 09/771,178

(22) Filed: Jan. 26, 2001

(65) Prior Publication Data

US 2002/0107494 A1 Aug. 8, 2002

(51) Int. Cl.[7] .................................................. A61F 13/15
(52) U.S. Cl. ................... 604/361; 604/385.18; 604/904
(58) Field of Search .................. 604/361, 904, 604/385.18

(56) References Cited

U.S. PATENT DOCUMENTS

| | | | |
|---|---|---|---|
| 3,756,238 A | 9/1973 | Hanke | 128/270 |
| 3,794,024 A | 2/1974 | Kokx et al. | 128/285 |
| 3,796,219 A | 3/1974 | Hanke | 128/285 |
| 4,317,454 A | 3/1982 | Bucalo | 128/759 |
| 5,647,863 A | 7/1997 | Hammons et al. | 604/378 |
| 5,649,914 A | 7/1997 | Glaug et al. | 604/361 |
| 5,681,298 A | 10/1997 | Brunner et al. | 604/361 |
| 5,702,376 A | 12/1997 | Glaug et al. | 604/361 |
| 5,728,125 A | 3/1998 | Salinas | 604/361 |
| 5,797,892 A | 8/1998 | Glaug et al. | 604/361 |
| 5,904,671 A | * 5/1999 | Navot et al. | 604/361 |
| 6,036,666 A | * 3/2000 | Peiler et al. | 604/11 |
| 6,063,042 A | * 5/2000 | Navot et al. | 600/584 |

FOREIGN PATENT DOCUMENTS

GB  1433415  4/1976

* cited by examiner

Primary Examiner—Dennis Ruhl
(74) Attorney, Agent, or Firm—Ohlandt, Greeley, Ruggiero & Perle, LLP

(57) ABSTRACT

There is provided a tampon that comprises an absorbent pledget and a menstrual fluid indicator associated therewith. The absorbent pledget has a proximal end that is placed near the cervical bone and a distal end opposite the proximal end. The indicator is preferably an additional layer formed in and in contact with the entire circumference of the absorbent pledget, and is located near the distal end. The indicator is designed to provide a sensory signal to the user that the capacity of the absorbent pledget of the tampon is exhausted, or just before by-pass leakage commences.

21 Claims, 1 Drawing Sheet

SIGNAL TAMPON

BACKGROUND OF THE INVENTION

1. Field of the Invention

The present invention relates generally to catamenial devices or tampons. More particularly, the present invention relates to catamenial devices or tampons adapted to provide a signal to the user. The present invention further relates to catamenial devices or tampons that signal the user upon exhaustion of the absorbent pledget, while providing a leakage protection benefit.

Women have to use a destructive test to ascertain whether a tampon has remaining absorbent capacity. Specifically, the tampon must be removed to determine whether it has been used to capacity. Even if not completely full, the tampon usually is not reinserted. Generally, a woman removes a tampon before it has reached its capacity in order to prevent an accident. Namely, if the capacity is exceeded, the excess menses flows, unimpeded from the vagina, to soil the user's clothing.

Presently, one criterion used for determining when to remove a tampon is elapsed time since insertion. The elapsed time criterion is not satisfactory for several reasons. The menstrual flow rate varies throughout the menstrual period. Thus, much of the absorbent capacity of a tampon is wasted due to the tendency to change the tampon to avoid accidental leakage. The flow variations throughout the menstrual period cause problems as to how long to use or wear a tampon since a woman cannot establish a definite time period in which the absorbent capacity of a tampon is sufficient. Additionally, a phenomenon, in which menses leaks before the tampon nears its full potential absorbency, occasionally occurs. This is generally known as by-pass leakage. This leakage is usually not predictable by the user's habitual wearing time. Therefore, a woman is in a quandary as to how long to wear the tampon during the varying menstrual flow days.

Larger and more absorbent tampons permit a woman to change tampons less often. However, larger tampons do not approach the goal of fully exhausting the absorbent capacity of the tampon, nor preventing accidents due to by-pass leakage.

2. Description of the Prior Art

Attempts have been made to provide a signal to a user when a sensory indicator is contacted by a body fluid. For example, U.S. Pat. Nos. 5,649,914, 5,702,376, and 5,797,892 issued to Glaug et al., on Jul. 22, 1997, Dec. 30, 1997, and Aug. 25, 1998, respectively, describe a toilet training aid. The aid is in the form of a pad that creates a temperature change sensation, a wet sensation, a dimensional change sensation, or a combination thereof when contacted by urine. Another example of a toilet training aid pad with a temperature change sensation signal is described in U.S. Pat. No. 5,681,298, to Brunner et al., that issued on Oct. 28, 1997.

There have been attempts to detect menstrual fluids. For example, U.S. Pat. No. 5,647,863, to Hammons et al., that issued on Jul. 15, 1997, describes a sanitary napkin. The napkin provides a signal by way of an indicator member that becomes noticeably stained when the storage capacity of the sanitary napkin is substantially exhausted. U.S. Pat. No. 5,728,125, to Salinas, that issued on Mar. 17, 1998, describes a sanitary napkin having a temperature-sensitive reactive chemical product that can respond by turning cold when it contacts and dissolves in a menstrual flow.

What is lacking and needed in the art is a tampon that provides the user with a signal when the tampon has reached its maximum absorbent capacity, or is about to leak, i.e. by-pass leakage, even though the tampon is not full.

SUMMARY OF THE INVENTION

It is an object of the present invention to provide a tampon that can be worn until essentially all of the absorbent capacity is exhausted.

It is also an object of the present invention to provide such a tampon that alerts the user when essentially all of the tampon's absorbent capacity is exhausted.

It is another object of the invention to provide such a tampon that alerts the user that by-pass leakage is about to occur.

It is also another object of the present invention to provide such a tampon that has a sensual, absorbent capacity signal associated therewith.

It is a further object of the present invention to provide such a tampon having additional leakage protection.

Accordingly, there is provided a tampon that comprises an absorbent pledget and a menstrual fluid indicator associated therewith. The absorbent pledget has a proximal end that is placed near the cervical bone and a distal end opposite the proximal end. The indicator is preferably an additional layer formed and in contact with the entire circumference of the absorbent pledget and is located near the distal end. The indicator is designed to provide a sensory signal to the user when the capacity of the absorbent pledget of the tampon is exhausted, or when by-pass leakage may occur.

DESCRIPTION OF THE INVENTION

Figure 1:
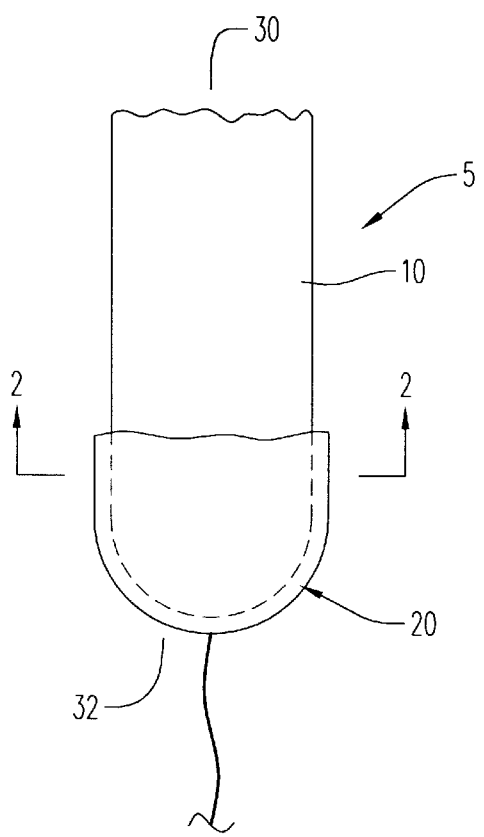
FIG. 1 is a partial plan view of the device of the present invention.

Referring to the drawings and, in particular, FIG. 1, there is provided a tampon generally represented by reference numeral 5. Tampon 5 has an absorbent pledget 10 and a menstrual fluid indicator 20 associated therewith. The absorbent pledget 10 has a proximal end 30 that is placed near the cervical bone and a distal end 32 opposite the proximal end 30.

Indicator 20 is preferably an additional layer that is in contact with the entire circumference of absorbent pledget 10, and is located near distal end 32. Indicator 20 extends a length from distal end 32 to proximal end 30, so that an effective surface area of absorbent pledget 10 is covered by indicator 20 to signal the user. Preferably, indicator 20 covers a length of about ⅛" to about 2" of absorbent pledget 10. More preferably, indicator 20 covers a length of about 1" of absorbent pledget 10.

Preferably, the indicator 20 is affixed to the circumference of absorbent pledget 10. The indicator 20 is designed to provide a sensory signal to the user that the capacity of absorbent pledget 10 of tampon 5 is exhausted. By way of example, indicator 20 may simply be an additional layer of carded or randoed web of rayon fiber, curly fiber, superabsorbent polymer (SAP) fiber, or combinations thereof.

Figure 2:
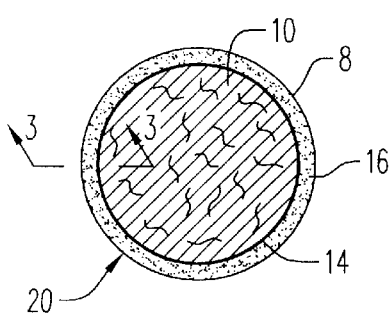
FIG. 2 is a sectional view taken along line 2—2 of FIG. 1.

Referencing FIG. 2, indicator 20 may have an inner film or non-woven material layer 14 that is positioned to contact absorbent pledget 10, a signal layer 16 that is positioned about layer 14, either directly or indirectly, and an outer film or non-woven material layer 8, either directly or indirectly about layer 16. A signal layer 16 is positioned between inner layer 14 and outer layer 8. The indicator 20 is activated by menstrual fluid such that the actuation of the indicator is perceivable to the user while tampon 5 remains within the vagina. Thus, indicator 20 becomes sensual to the user when wetted by menstrual fluid thereby avoiding removal of tampon 5 until essentially the entire capacity of absorbent pledget 10 is exhausted, yet alerting the user that by-pass leakage is about to commence and, thus, it can be avoided.

To prevent premature activation of the signal layer 16 due to the inherent moisture in the vagina, the outer layer 8 may be made of an impermeable or semi-impermeable material. Suitable impermeable or semi-impermeable materials, include, for example, typical coverstocks used in the absorbent product industry with a hydrophobic nature, such as those used as an outer backing on diapers and sanitary pads or apertured films such as Dry Weave, or films used on catamenial products, e.g. carded thermal bonded polypropylene, polyester, or polyethylene fiber, epoxy, nitrocellulose, spun bonded fabrics, such as, polyethylene/polypropylene, hydrophobically treated spun bond, meltblown, or paper web, and combinations thereof.

The inner layer 14 may include any of the typical coverstocks used in the absorbent product industry, such as diapers, sanitary products, adult incontinence products, and the like. Said coverstocks include, but are not limited to, adhesive bonded polyester fiber, carded thermal bonded polypropylene, polyethylene, or bicomponent fiber, meltblown non-woven fabric, bicomponent spun bonded fabrics, such as polyethylene/polypropylene, or any combinations thereof.

Activation of the signal layer 16 results from menstrual fluid penetrating the inner layer 14 that directly contacts absorbent pledget 10.

Figure 3:
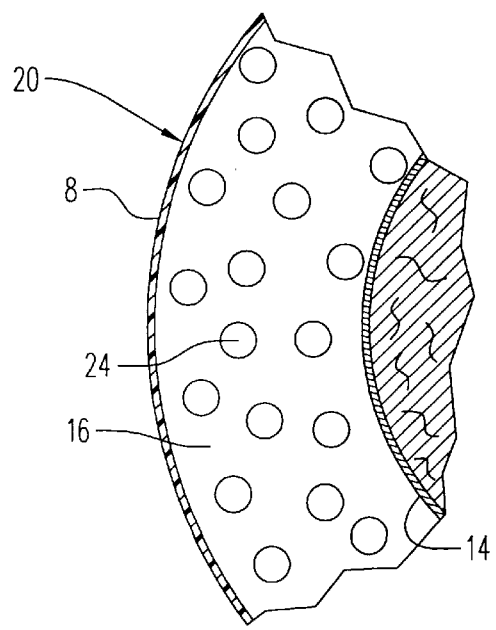
FIG. 3 is a sectional view of one example taken along line 3—3 of FIG. 2.

Referring to FIG. 3, signal layer 16 has a sensory material 24, which reacts in the presence of menstrual fluid. The sensory material 24 may be made of fibers or materials that tend to "spring open", or swell, in the presence of moisture. Suitable fibers or materials include, for example, curly fiber, cellulosic sponge, a swellable adsorbent material such as super absorbent polymer (SAP) or hydrogel, or any combination of these materials. The "opening" or swelling of these materials in indicator 20, and the resulting sensation of pressure, signal the user that the capacity of absorbent pledget 10 of tampon 5 is exhausted, or that by-pass leakage may occur. Suitable super absorbent fiber includes, for example, cross-linked acrylate copolymer fiber.

In addition to signaling the user, the curly fiber, cellulosic sponge, SAP, or hydrogel in indicator 20 may provide further leakage protection due to their "opening" and swelling properties. Therefore, even if the user fails to or is unable to immediately remove and replace the tampon upon being signaled that it should be removed, this added leakage protection feature serves as a further preventative measure against by-pass leakage.

In one embodiment, the sensory material 24 may also include exothermic materials that release heat upon exposure to moisture. Thus, when menstrual fluid contacts indicator 20, heat is released producing a sensation of warmth, signaling the user that the capacity of absorbent pledget 10 of tampon 5 is exhausted, or that by-pass leakage may occur. Suitable exothermic materials include, for example, Cabsorb ZS500A, an exothermic zeolite provided by GSA, glycerin, and mixtures thereof.

In another embodiment, the sensory material 24 may also include a material that produces a cold sensation. As menstrual fluid contacts indicator 20, a cold sensation is produced signaling the user that the capacity of absorbent pledget 10 of tampon 5 is exhausted, or that by-pass leakage may occur. Suitable materials that produce a cold sensation when contacted with menstrual fluid include, for example, menthyl lactate sold under the tradename Frescolat ML by H&R Florasynth, menthol, ethanol, or any combinations thereof.

In a third embodiment, the sensory material 24 may also include a gas-releasing material. As menstrual fluid contacts indicator 20, gas is released that produces a "fizzy" sensation signaling the user that the capacity of absorbent pledget 10 of tampon 5 is exhausted, or that the tampon is about to leak. Suitable gas releasing materials include, for example, sodium bicarbonate.

In a fourth embodiment, the sensory material 24 may also include an encapsulated fragrance-releasing material. As menstrual fluid contacts indicator 20, the encapsulated fragrance is released signaling the user that the capacity of absorbent pledget 10 of tampon 5 is exhausted, or that by-pass leakage may commence.

In a fifth embodiment, the sensory material 24 may also include a color producing material. As menstrual fluid contacts indicator 20, a distinct color is produced signaling the user that the capacity of absorbent pledget 10 of tampon 5 is exhausted, or that by-pass leakage may commence.

In addition, encapsulation is not limited to fragrance. Each and every sensory material described above may be present in an encapsulated form, either alone or in combination. As menstrual fluid contacts the encapsulated sensory material, the sensory material is released, signaling the user that the capacity of absorbent pledget 10 of tampon 5 is exhausted, or that by-pass leakage may occur.

When the sensory material is not a fiber, the signal layer may include a fibrous web having sensory material 24 incorporated therein.

The present invention having been thus described with particular reference to the preferred forms thereof, it will be obvious that various changes and modifications may be made therein without departing from the spirit and scope of the present invention as defined in the appended claims.

Wherefore I claim:

1. A tampon comprising:
    an absorbent pledget with a proximal end for placement near the cervical bone and a distal end opposite said proximal end; and
    a menstrual fluid indicator in contact with said absorbent pledget at said distal end, said indicator being sensually perceivable to a user when contacted by said menstrual fluid, said indicator having:
        an inner layer in contact with said absorbent pledget;
        an outer layer impermeable to moisture inherent within a vagina; and
        a signal layer contained between said inner and outer layers.

2. The tampon of claim 1, wherein said inner layer is made of materials selected from the group consisting of adhesive bonded polyester fiber, carded thermal bonded polypropylene, polyethylene, and bicomponent fiber, meltblown non-woven fabric, bicomponent spun bonded polyethylene/polypropylene, bicomponent spun bonded fabrics, and any combinations thereof.

3. The tampon of claim 2, wherein said inner layer is made from bicomponent spun bonded polyethylene/polypropylene.

4. The tampon of claim 1, wherein said outer layer is made from materials selected from the group consisting of carded thermal bonded polypropylene, polyester, and polyethylene, epoxy, nitrocellulose, spun bonded polyethylene/polypropylene, spun bonded fabric, hydrophobically treated spun bond, meltblown, and paper web, and any combinations thereof.

5. The tampon of claim 4, wherein said outer layer is bicomponent spun bonded polyethylene/polypropylene.

6. The tampon of claim 1, wherein said signal layer comprises a sensory material that reacts in the presence of said menstrual fluid.

7. The tampon of claim 6, wherein said sensory material is a spring open material selected from the group consisting of carded or randoed rayon, curly fiber, cellulosic sponge, and any combinations thereof.

8. The tampon of claim 7, wherein said fiber is curly fiber.

9. The tampon of claim 6, wherein said sensory material is encapsulated.

10. The tampon of claim 6, wherein said sensory material is selected from the group consisting of a swelling material, exothermic material, cold sensation material, gas-releasing material, fragrance-releasing material, color producing material, and any combinations thereof.

11. The tampon of claim 10, wherein said swelling material is selected from the group consisting of: superabsorbent polymer, hydrogel, and mixtures thereof.

12. The tampon of claim 11, wherein said swelling material is superabsorbent polymer.

13. The tampon of claim 12, wherein said super absorbent polymer is a cross-linked acrylate copolymer fiber.

14. The tampon of claim 10, wherein said exothermic material is selected from the group consisting of: exothermic zeolites, glycerin, and mixtures thereof.

15. The tampon of claim 14, wherein said exothermic material is exothermic zeolite.

16. The tampon of claim 10, wherein said cold sensation material is selected from the group consisting of menthyl lactate, menthol, ethanol, and any combinations thereof.

17. The tampon of claim 16, wherein said cold sensation material is menthol.

18. The tampon of claim 10, wherein said gas-releasing material is sodium bicarbonate.

19. The tampon of claim 10, wherein said sensory material is contained within a fibrous web.

20. A method for avoiding by-pass leakage comprising:
   (a) providing a tampon having an absorbent pledget and a menstrual fluid indicator in contact with said pledget, whereby said indicator is sensually perceivable to a user when contacted with menstrual fluid, said indicator having:
      an inner layer in contact with said absorbent pledget;
      an outer layer impermeable to moisture inherent within a vagina; and
      a signal layer contained between said inner and outer layers; and
   (b) removing said tampon once said user sensually perceives said indicator.

21. The tampon of claim 20, wherein said sensory material is selected from the group consisting of spring open fiber, swelling material, exothermic material, cold sensation material, gas-releasing material, fragrance-releasing material, color producing material, and any combinations thereof.

* * * * *